United States Patent [19]

Nezat

[11] Patent Number: 4,520,013

[45] Date of Patent: May 28, 1985

[54] TOPICAL PREPARATION AND METHOD FOR USING SAME IN TREATING SKIN DISORDERS IN ANIMALS

[75] Inventor: Jerry W. Nezat, Kalispell, Mont.

[73] Assignee: Creative Research and Development, Inc., Whitefish, Mont.

[21] Appl. No.: 474,165

[22] Filed: Mar. 10, 1983

[51] Int. Cl.$^3$ .............................................. A61K 33/34
[52] U.S. Cl. .................................... 424/141; 424/143; 514/122
[58] Field of Search ................................ 424/141, 213

[56] References Cited

U.S. PATENT DOCUMENTS 3,144,382  8/1964  Di Scala ............................. 424/213

*Primary Examiner*—Sam Rosen
*Attorney, Agent, or Firm*—Thomas R. Vigil

[57] ABSTRACT

The topical preparation is utilized in treating skin disorders such as skin infections, minute insect infestations, and rashes in the skin of living creatures such as dogs, cats and sheep. One preferred embodiment of the preparation comprises a solution including the following ingredients: approximately 0.8 ounce malathion; approximately 5 ounces copper sulfate; approximately 5 ounces alum; approximately 10 ounces salt; approximately 1 ounce chloroform; approximately 3 quarts 70% alcohol solution; approximately 0.04 ounce Au Jus mix (powdered); and approximately 5 gallons of water.

The method for utilizing the solution defining the topical preparation includes the steps of: applying ½ cup of the solution, full strength, to the body of the living creature and rubbing it in; applying another ½ cup of the solution, full strength, to the body of the animal one week later and rubbing it in; and applying ½ cup of the solution, full strength, to the body of the animal two weeks after the first application and rubbing it in.

31 Claims, No Drawings

TOPICAL PREPARATION AND METHOD FOR USING SAME IN TREATING SKIN DISORDERS IN ANIMALS

BACKGROUND OF THE INVENTION

1. Field of the Invention

The present invention relates to topical preparations which are applied to animals for treating skin disorders, such as skin infections, minute insect infestations and rashes. More particularly, the topical preparation of the present invention is used in treating mite infestation in living creatures such as cats, dogs and sheep.

2. Description of the Prior Art

Heretofore, the substance malathion has been used for treating mite infestation in animals, such as cats, dogs and sheep. However, the malathion has not always been effective in the dosages in which it has been applied to the skin of animals. To enhance the effectiveness of malathion, larger concentrations of the malathion in a water solution have been applied to the skin of animals. To some extent, an increased dosage or concentration of malathion has resulted in a higher percentage of eradication of the mite infestation but not 100% eradication.

Although one can further increase the amount of malathion being used, there are certain limits on the amount of malathion that can be used, since malathion is a known carcinogenic agent. Also, too much malathion appears to cause a temporary dysfunction in the animal being treated.

In addition to mites, malathion has been used to kill the Mediterranean fruit fly.

Further, it has been known to use copper sulfate as an internal veterinary pharmaceutical. Examples of such internal veterinary pharmaceutical uses of copper sulfate are disclosed in the Knapp, Jr. U.S. Pat. No. 3,422,182 and the Scroggs U.S. Pat. No. 3,489,385.

Also it has been stated in Chemical Abstract CA 67:90034 reporting on a 1967 article in a Russian publication directed to the compatibility of organophosphorus insecticides with fungicides, that the insecticidal properties of various elements including karbofos, which is equivalent to malathion, was decreased when used in a mixture with copper sulfate.

Further in Chemical Abstract CA 74:86808 reporting on a 1971 Czechoslovakian publication, it is stated that pesticide or fungicide solutions that were applied as films on plants or plant seeds, can be prepared by embedding the active substances such as malathion or copper sulfate ($CuSO_4$) in solutions of hydrophilic synthetic polymers capable of swelling in water. However, there is no teaching in this Abstract that $CuSO_4$ and malathion should be combined.

As will be described in greater detail hereinafter, the present invention differs from the previously proposed use of malathion for treating skin disorders in animals such as mite infestation, by providing a solution of water, malathion and copper sulfate with the level of malathion being low enough to prevent temporary dysfunction of the animal and hopefully low enough so as not to be a cancer causing agent, and yet, having its effectiveness for killing mites or other insects, bacteria or surface viruses enhanced by the addition of the copper sulfate, and with the copper sulfate in the solution being at a level low enough so that it will not cause any burning to the skin of the animal and yet high enough to provide an enhanced effectiveness of the combination of malathion and copper sulfate in killing mites or other insects, bacteria or surface viruses infesting or infecting the skin of animals, such as cats, dogs or sheep.

SUMMARY OF THE INVENTION

According to the invention there is provided a topical preparation adapted for application to the skin of living creatures for treating skin disorders, such as infections, minute insect infestations and rashes, in the skin of living creatures, such as cats, dogs and sheep, said preparation comprising a solution having the following ingredients: between approximately 3 and approximately 12 gallons of water, between approximately 0.2 ounce and 5 ounces of malathion in an amount which is large enough to be effective in treating mite infestation but which is small enough so as to have little or no carcinogenic effect, between approximately 0.5 ounce and approximately 10 ounces of copper sulfate in an amount which is large enough to be effective in treating mite infestation but which is small enough as not to cause burning of the skin.

Further according to the invention in one preferred embodiment there is provided a topical preparation for treating skin fections, minute insect infestations and rashes in the skin of living creatures such as cats, dogs and sheep, said preparation comprising a solution including the following ingredients: approximately 0.8 ounce malathion, approximately 5 ounces copper sulfate, approximately 5 ounces alum, approximately 10 ounces salt, approximately 1 ounce chloroform, approximately 3 quarts 70% alcohol solution, approximately 0.04 ounce Au Jus mix (powdered), and approximately 5 gallons of water.

Still further according to the invention there is provided a method for treating skin disorders such as skin infections, minute insect infestations and rashes in the skin of living creatures such as cats, dogs and sheep using a topical preparation as described above comprising a solution of several ingredients, said method comprising the steps of applying ½ cup of said solution full strength to the skin of the creature and rubbing it in thoroughly over the whole body of the creature; one week later applying another ½ cup of the solution full strength to the body of the creature and rubbing the solution into the hair of the creature; and two weeks later applying a third ½ cup of the solution full strength to the body of the living creature and rubbing it thoroughly into the hair of the creature.

DESCRIPTION OF THE PREFERRED EMBODIMENTS

According to the teachings of the present invention, a topical preparation comprising a solution of water, malathion and copper sulfate is prepared and is applied to the skin of animals that have skin disorders such as skin infections, infestation of the skin by minute insects such as mites, and rashes.

More specifically, the topical preparation of the present invention can be utilized in treating mites, ringworm, mange, ticks, fleas, skin rashes and ear infections.

The primary ingredients of the solution forming the topical preparation of the present invention have the following ratios: between approximately 3 and approximately 10 gallons of water; between approximately 0.2 ounce and approximately 5 ounces of malathion; and between approximately 0.5 ounce and approximately 10 ounces of copper sulfate.

In a preferred embodiment of the topical preparation of the present invention, the proportion of malation is approximately 0.8 ounce malathion, the proportion of copper sulfate is approximately 5 ounces of copper surface and the proportion of water is approximately 5 gallons of water.

Additionally, it has been found that the effectiveness of the topical preparation and the amount needed in treating an animal, more specifically, the amount needed in an application to the skin of an animal, and the amount of applications needed to obtain 100% eradication of mite infestation, has been found to be enhanced by the addition of other elements to the topical preparation. These elements are as follows: alum, salt (sodium chloride), chloroform, 70% alcohol solution and a flavoring.

After many experimental tests, it was found that between approximately 0.5 ounce and approximately 20 ounces of alum added to the topical preparation enhanced its effectiveness. Also from such empirical tests it was determined that 5 ounces of alum is preferred.

Again, after many tests, it was found that between approximately 1 ounce and approximately 20 ounces of salt enhanced the effectiveness of the topical preparation and that a preferred quantity of salt is approximately 10 ounces of salt.

Again, numerous tests showed that between approximately 0.25 ounce and approximately 2 ounces of chloroform enhanced the effectiveness of the topical preparation and that a preferred amount appeared to be approximately 1 ounce of chloroform.

Still further tests showed that between approximately 1 quart and approximately 6 quarts of 70% alcohol solution enhanced the effectiveness of the topical preparation and after a number of empirical tests, it was determined that a desired effectiveness of the preparation was obtained with 3 quarts of 70% alcohol solution.

Additionally, various types of flavoring such as boullion, Au Jus powder and blood were utilized and it was found that the best results were obtained with a meat flavoring of approximately 0.04 ounce of powdered Au Jus mix.

The site of the mite infestation is often raw, and it is believed that the salt and alcohol help to prevent infections of the lesions caused by mite infestation while the mites are being killed by the malathion and copper sulfate. Also, it is believed that the alcohol serves as a wetting agent and enables the solution of the topical preparation to penetrate through matted hair of the animal.

Although not known with complete certainty, it is believed that the Au Jus mix tends to attract mites from their position under the skin and when they encounter the solution, the chloroform serves to immobilize the activity of the mites. The alum acts as a drying agent to assist the salt and alcohol in healing of the lesions.

In use, it has been found that ½ cup of the preferred solution, full strength, is all that is needed for one application to an average size dog. In practicing the method of the present invention, utilizing the topical preparation of the present invention, ½ cup of the solution is applied all over the body of an average size dog, and particularly, to the infected area. This can be done by using ½ cup of the solution full strength applied directly to the infected areas, and then covering the rest of the body with a diluted mixture of ½ cup of the topical preparation and ½ cup of water.

It is noted that the ingredients of the solution are such as to cause irritation to human skin, and accordingly, rubber gloves are worn when applying the solution and rubbing the solution into the hair of the animal, thereby to protect the hands of the person applying the solution. Also, with respect to ear infections, a cotton swab is dipped into the topical preparation, full strength, and applied to the inside of the ear.

The application of the topical preparation to the skin and hair of the animal is repeated one week later and then repeated again a second week later, so that in all, three applications are made to make certain the mite infestation is completely eradicated.

Again, by keeping the concentration of the malathion to no more than 5 ounces and preferably only 0.8 ounce, one is able to stay away from the carcinogenic propensities of malathion which for 5 gallons of water, appears to present a dangerous level at 4–5 ounces of malathion. In fact, in order to meet Federal Drug Administration approval, the amount of malathion should be less than 4 ounces per 5 gallons of water.

The topical preparation, or more particularly, the solution forming the topical preparation, of the present invention, has been found to have indefinite shelf life, provided it is in a liquid-tight and air-tight sealed container. The fumes from the solution could be deleterious to humans so that in use, one must be cautioned not to breathe the fumes from the topical preparation when applying it to the skin of an animal.

The topical preparation, and more particularly, the solution of the preparation having the ingredients described above, has been found to be 100% effective in treating mite infestation and other skin disorders such as ringworm, mange, ticks, fleas, skin rashes, ear infections, etc., encountered by animals such as cats, dogs and sheep.

From the foregoing description, it will be apparent that the topical preparation of the present invention and the method of applying same, have a number of advantages, some of which have been described above and others of which are inherent in the invention. Accordingly, the scope of the invention is only to be limited as necessitated by the accompanying claims.

I claim:

1. A topical preparation adapted for application to the skin of animals for treating mite infestation in animals including dogs, cats and sheep, said preparation comprising a solution having the following ingredients: between approximately three and approximately twelve gallons of water; between approximately 0.2 ounce and 5 ounces of malathion in an amount which is large enough to be effective in treating mite infestation but which is small enough so as to have little or no carcinogenic effect, and between approximately 0.5 ounce and approximately 10 ounces of copper sulfate in an amount which is large enough to be effective in treating mite infestation but which is small enough as not to cause burning of the skin.

2. The topical preparation of claim 1 wherein said solution comprises approximately 0.8 ounce malathion.

3. The topical preparation of claim 1 wherein said solution comprises approximately 5 ounces of copper sulfate.

4. The topical preparation of claim 1 wherein said solution comprises approximately 5 gallons of water.

5. The topical preparation of claim 1 wherein said solution comprises approximately 0.8 ounce malathion, approximately 5 ounces of copper sulfate and approximately 5 gallons of water.

6. The topical preparation of claim 1 which further comprises between approximately 0.5 ounce and approximately 20 ounces of alum.

7. The topical preparation of claim 6 wherein said solution includes approximately 5 ounces of alum.

8. The topical preparation of claim 1 further including between approximately 1 ounce and approximately 20 ounces of salt.

9. The topical preparation of claim 8 wherein said solution includes approximately 10 ounces of salt.

10. The topical preparation of claim 1 further including between approximately 0.25 ounce and approximately 2 ounces of chloroform.

11. The topical preparation of claim 10 wherein said solution includes approximately 1 ounce of chloroform.

12. The topical preparation of claim 1 further including between approximately 1 quart and approximately 6 quarts of 70% alcohol solution.

13. The topical preparation of claim 12 wherein said solution includes approximately 3 quarts of 70% alcohol solution.

14. The topical preparation of claim 1 further including a quantity of meat flavoring.

15. The topical preparation of claim 14 wherein said flavoring is approximately 0.04 ounce of powdered Au Jus mix.

16. A method for treating mite infestation in living creatures including dogs, cats and sheep utilizing the solution defining the topical preparation of claim 1 and including the steps of: applying ½ cup of the solution, full strength, to the body of the living creature and rubbing it in; applying another ½ cup of the solution, full strength, to the body of the animal one week later and rubbing it in; and applying ½ cup of the solution, full strength, to the body of the animal two weeks after the first application and rubbing it in.

17. The method of claim 16 wherein ½ cup of said solution is applied, full strength, to the infested areas of the animal's body and ½ cup of said solution mixed with ½ cup of water is applied to the remaining areas of the animal's body on each application.

18. A method for treating mite infestation in living creatures including dogs, cats and sheep utilizing the topical preparation defined in claim 5 and including the steps of: applying ½ cup of the solution of the preparation, full strength, to the body of an animal and rubbing it in; one week later, applying another ½ cup of the solution, full strength, to the body of the animal and rubbing it in; and applying ½ cup of the solution, full strength, to the body of the animal and rubbing it in two weeks after the first application.

19. The method of claim 18 wherein ½ cup of said solution is applied full strength to the infected areas of the animal's body and ½ cup of said solution mixed with ½ cup of water is applied to the remaining areas of the animal's body on each application.

20. A topical preparation for treating mite infestation in living creatures, including dogs, cats and sheep, said preparation comprising a solution including the following ingredients: approximately 0.8 ounce malathion; approximately 5 ounces copper sulfate; approximately 5 ounces alum; approximately 10 ounces salt; approximately 1 ounce chloroform; approximately 3 quarts 70% alcohol solution; approximately 0.04 ounce Au Jus mix (powdered); and approximately 5 gallons of water.

21. A method for treating mite infestation in living creatures including dogs, cats and sheep utilizing the topical preparation defined in claim 20 and including the steps of: applying ½ cup of the solution of the preparation, full strength, to the body of a living creature and rubbing it in; applying another ½ cup of the solution, full strength, to the body of the living creature and rubbing it in one week later; and applying ½ cup of the solution, full strength, to the body of the animal and rubbing it in two weeks after the first application.

22. The method of claim 21 wherein ½ cup of said solution is applied, full strength, to the infested areas of the animal's body and ½ cup of said solution mixed with ½ cup of water is applied to the remaining areas of the animal's body on each application.

23. A topical preparation adapted for application to the skin of animals for treating skin disorders including skin infection, minute insect infestation and rashes in the skin of animals including dogs, cats and sheep, said preparation comprising a solution having the following ingredients: between approximately three and approximately twelve gallons of water; between approximately 0.2 ounce and 5 ounces of malathion in an amount which is large enough to be effective in treating mite infestation but which is small enough so as to have little or no carcinogenic effect; and between approximately 0.5 ounce and approximately 10 ounces of copper sulfate in an amount which is large enough to be effective in treating mite infestation but which is small enough as not to cause burning of the skin.

24. The topical preparation of claim 23 wherein said solution comprises approximately 0.8 ounce malathion, approximately 5 ounces of copper sulfate and approximately 5 gallons of water.

25. A topical preparation for treating skin disorders such as skin infections, minute insect infestations, and rashes in the skin of living creatures including dogs, cats and sheep, said preparation comprising a solution including the following ingredients: approximately 0.8 ounce malathion; approximately 5 ounces copper sulfate; approximately 5 ounces alum; approximately 10 ounces salt; approximately 1 ounce chloroform; approximately 3 quarts 70% alcohol solution; approximately 0.04 ounce Au Jus mix (powdered); and approximately 5 gallons of water.

26. A method for treating skin disorders such as infection, minute insect infestation and rashes in the skin of living creatures including dogs, cats and sheep utilizing the solution defining the topical preparation of claim 23 and including the steps of: applying ½ cup of the solution, full strength, to the body of the living creature and rubbing it in; applying another ½ cup of the solution, full strength, to the body of the animal one week later and rubbing it in; and applying ½ cup of the solution, full strength, to the body of the animal two weeks after the first application and rubbing it in.

27. The method of claim 26 wherein ½ cup of said solution is applied, full strength, to the infested areas of the animal's body and ½ cup of said solution mixed with ½ cup of water is applied to the remaining areas of the animal's body on each application.

28. A method for treating skin disorders such as infection, minute insect infestation and rashes in the skin of living creatures including dogs, cats and sheep utilizing the topical preparation defined in claim 24 and including the steps of: applying ½ cup of the solution of the preparation, full strength, to the body of a living creature and rubbing it in; applying another ½ cup of the solution, full strength, to the body of the living creature and rubbing it in one week later; and applying ½ cup of the solution, full strength, to the body of the animal and rubbing it in two weeks after the first application.

29. The method of claim 28 wherein ½ cup of said solution is applied, full strength, to the infested areas of the animal's body and ½ cup of said solution mixed with ½ cup of water is applied to the remaining areas of the animal's body on each application.

30. A method for treating skin disorders such as infection, minute insect infestations and rashes in the skin of living creatures including dogs, cats and sheep utilizing the solution defining the topical preparation of claim 25 and including the steps of: applying ½ cup of the solution, full strength, to the body of the living creature and rubbing it in; applying another ½ cup of the solution, full strength to the body of the animal one week later and rubbing it in; and applying ½ cup of the solution, full strength, to the body of the animal two weeks after the first application and rubbing it in.

31. The method of claim 30 wherein ½ cup of said solution is applied, full strength, to the infested areas of the animal's body and ½ cup of said solution mixed with ½ cup of water is applied to the remaining areas of the animal's body on each application.

* * * * *